(12) United States Patent
Furumi et al.

(10) Patent No.: US 7,285,604 B2
(45) Date of Patent: Oct. 23, 2007

(54) PROCESS FOR PRODUCTION OF MOLECULAR DEVICES

(75) Inventors: Seiichi Furumi, Koganei (JP); Akira Otomo, Koganei (JP); Shinro Mashiko, Koganei (JP)

(73) Assignee: National Institute of Information and Communications Technology, Incorporated Administrative Agency, Tokyo (JP)

( * ) Notice: Subject to any disclaimer, the term of this patent is extended or adjusted under 35 U.S.C. 154(b) by 225 days.

(21) Appl. No.: 10/509,380

(22) PCT Filed: Mar. 26, 2003

(86) PCT No.: PCT/JP03/03669

§ 371 (c)(1),
(2), (4) Date: Sep. 27, 2004

(87) PCT Pub. No.: WO03/082954

PCT Pub. Date: Oct. 9, 2003

(65) Prior Publication Data

US 2005/0215731 A1    Sep. 29, 2005

(30) Foreign Application Priority Data

Mar. 28, 2002  (JP)  ............... 2002-091548
Mar. 29, 2002  (JP)  ............... 2002-094211

(51) Int. Cl.
C08G 73/02   (2006.01)
C08G 73/56   (2006.01)
C08G 83/00   (2006.01)

(52) U.S. Cl. ..................... 525/540; 525/540
(58) Field of Classification Search ............. 525/540
See application file for complete search history.

(56) References Cited

FOREIGN PATENT DOCUMENTS

| EP | 899 286 | 3/1999 |
|---|---|---|
| JP | 2000-026597 | 1/2000 |
| JP | 2000-063513 | 2/2000 |
| JP | 2003-95999 | 4/2003 |

OTHER PUBLICATIONS

Johan F. G. A. Jansen et al.; Science, vol. 266, pp. 1226-1229, Nov. 18, 1994. Cited in the specification.
A. I. Cooper et al.; Letters to Nature, vol. 389, pp. 368-371, Sep. 25, 1997. Cited in the specification.

*Primary Examiner*—Duc Truong
(74) *Attorney, Agent, or Firm*—Westerman, Hattori, Daniels & Adrian, LLP.

(57) ABSTRACT

An object of the present invention is to provide a method of effectively producing a nano-particle and a nano-wire, and others.

Specifically, the present invention provides a method of producing a molecular device including: the use of a molecular structure having a higher atomic density in the periphery than in the interior and bonding residues in the periphery; and a step of crosslinking the bonding residues, and the method of producing a molecular device according to claim 1, characterized in that the molecular structure is constituted by a skeleton portion having a skeleton structure, and a terminal portion which is arranged in the outer shell of the skeleton portion, has a higher atomic density than that of the skeleton portion and has bonding residues; and that in the step of crosslinking the bonding residues, the bonding residues in the terminal portion of the molecular structure are crosslinked to form the molecular structure into a shell structure, and others.

4 Claims, 7 Drawing Sheets a          b a          b a   b a b the first generation (n = 1)

the third generation (n = 3)

the fifth generation (n = 5)

PROCESS FOR PRODUCTION OF MOLECULAR DEVICES

TECHNICAL FIELD

The present invention relates to a method of producing a molecular aggregate of which the linked form is controlled in a molecular level, by irradiating a molecular structure having a bonding residue in the periphery with light, and through taking advantage of the photochemical process and the photophysical process, selectively and effectively combining the periphery of the molecule or mutual molecular structures. By applying the present technique, it becomes easy to make various three-dimensional molecular devices of highly dense molecules.

BACKGROUND ART

The present silicon semiconductor element has remarkably improved the ability of computers by its hyperfine structure and integrated structure into high density. In the silicon semiconductor elements, an n-type or p-type semiconductor is made by doping a very small amount of impurities into silicon. However, by a progress of hyperfine processing, the number of impurity atoms contained in one element has been extremely decreased, and as a result, the element cannot work as a semiconductor any longer in principle. The dimension of the element considered to be the limit is a plurality of tens of nm, and if a hyperfine processing technology advances at a current pace, it is predicted that the limit will be reached after a plurality of tens of years.

In a fine processing technology by optical lithography using a chemical amplification type photo resist, the applied light has been shifted from visible light to ultraviolet light or deep ultraviolet light, but the limit of resolution is considered to be about 70 nm. Recently, an application of lithography using an X-ray, a focused ion beam and an electron beam, which have shorter radiation wavelengths has been investigated. However, in order to use these radiation wavelengths, the development of a new photo resist, an electron beam resist, an optical system and a mask, and the reduction of a manufacturing cost are necessary and expected. However, the technical and practical problems have not been improved yet at this stage. Accordingly, the technology based on a top-down concept reaches a limit.

As for a technology based on a bottom-up concept, a technique using a scanning probe microscope captures attention at present. One of the technologies can make a nanometric structure by disposing and reacting atoms or molecules in an arbitrary place with the use of a scanning tunneling microscope (STM). The study is described, for instance, in a scientific magazine, Nature, 409, 683 (2001) by Y. Okawa and M. Aono. Another technology has succeeded in the production of a self-organization film which is patterned in a nanometric order, by drawing the pattern on a substrate with a solution of thiol molecules coated on the top of a fine needle in an atomic force microscope (AFM). The study is described, for instance, in a scientific magazine, Science, 283, 661 (1999) by R. D. Piner, J. Zhu, F. Xu, S. Hong and C. A. Mirkin. Both technologies are excellent techniques for making a two-dimensional structure in a nanometric region, but are difficult to construct a three-dimensional structure, and are not practical from the viewpoint of a manufacturing cost.

The above-described methods for making a device are based on the concept of the so-called top-down technology, and have difficulty in producing a three-dimensional molecular device having a smaller size.

At present, a new molecular device of highly dense molecules, which can be operated even though having a dimension of a nanometric level, is energetically developed in a worldwide scale. For instance, a single electron element capable of controlling the switching on and off with one electron, and a molecular device using a functional organic molecule as a molecular structure are proposed. In order to put the molecular devices based on new concepts to practical use, many problems must be still solved. One big problem among them is how to selectively combine individual molecules. This is the big problem of the bottom-up technique, and is mentioned in Nikkei Science of a scientific magazine, 2001, December, page 37. However, an effective method for controlling the coupling of individual molecular elements has not been found until now.

DISCLOSURE OF THE INVENTION

As a result of intensive research for the purpose of solving the above described problems, the present inventors have found that each molecular structure necessary in making a molecular device of highly dense molecules, can be combined by photoirradiation or the like. At least one problem out of the above described problems is solved by the invention described below.

(1) The first invention according to the present application is "a method of producing a molecular device including: the use of a molecular structure having a higher atomic density in the periphery than in the interior and bonding residues in the periphery; and a step of crosslinking the bonding residues". For instance, a dendrimer has a higher atomic density in the periphery (the branch part) than in the interior (so-called the core part). In the present invention, a molecular device is produced by thus using a molecular structure having bonding residues in the periphery (the outside region) among molecular structures having more atoms in the outside region of a molecule than in the vicinity of the center of the molecule, and crosslinking (including combining) the above described bonding residues. By crosslinking the bonding residues in a molecular structure, nano-particles and nano-wires can be produced, and by using these, a molecular device having functional molecular structures and functional molecular aggregates assembled at a high density, can be produced.

(2) Another invention according to the present application is "the method of producing a molecular device according to the item (1), characterized in that the molecular structure is constituted by a skeleton portion having a skeleton structure, and a terminal portion which is arranged in the outer shell of the skeleton portion, has a higher atomic density than that of the skeleton portion and has bonding residues; and that in the step of crosslinking the bonding residues, the bonding residues in the terminal portion of the molecular structure are crosslinked to form a shell structure in the molecular structure". The molecular structure thus acquiring the shell structure is also called a nano-particle. The nano-particle has a space in a shell, and can include various materials.

(3) Another invention according to the present application is "the method of producing a molecular device according to the item (1) or (2), wherein the bonding residue is an optically bonding residue". Because the bonding residue is the optically bonding residue, the reaction can be controlled by photoirradiation.

(4) Another invention according to the present application is "the method of producing a molecular device according to any one of the item (1), (2) or (3), wherein the bonding residue has at least one of one or both of a double bond and a triple bond".

(5) Another invention according to the present application is "the method of producing a molecular device according to the item (1) or (2), wherein the bonding residue is any one of a cinnamic acid group, an α-cyano cinnamic acid group, a coumalin group, a chalcone group, a cinnamylidene acetate group, a p-phenylene diacrylate group, an acetylene group, a diacetylene group, a diphenyl acetylene group and an anthracene group". These groups are effectively coupled, and are effective for crosslinking such as intramolecular coupling and intermolecular coupling.

(6) Another invention according to the present application is "the method of producing a molecular device according to any one of the items (1) to (5), wherein the molecular structure is a dendrimer".

(7) Another invention according to the present application is "the method of producing a molecular device according to the item (6), wherein the dendrimer is expressed by the following formula (I) or (II)":

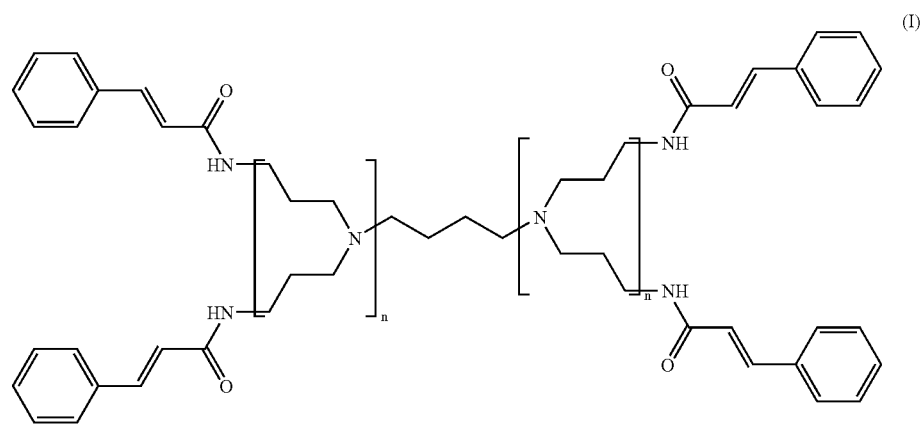

wherein n represents an integer of 10 or less, and

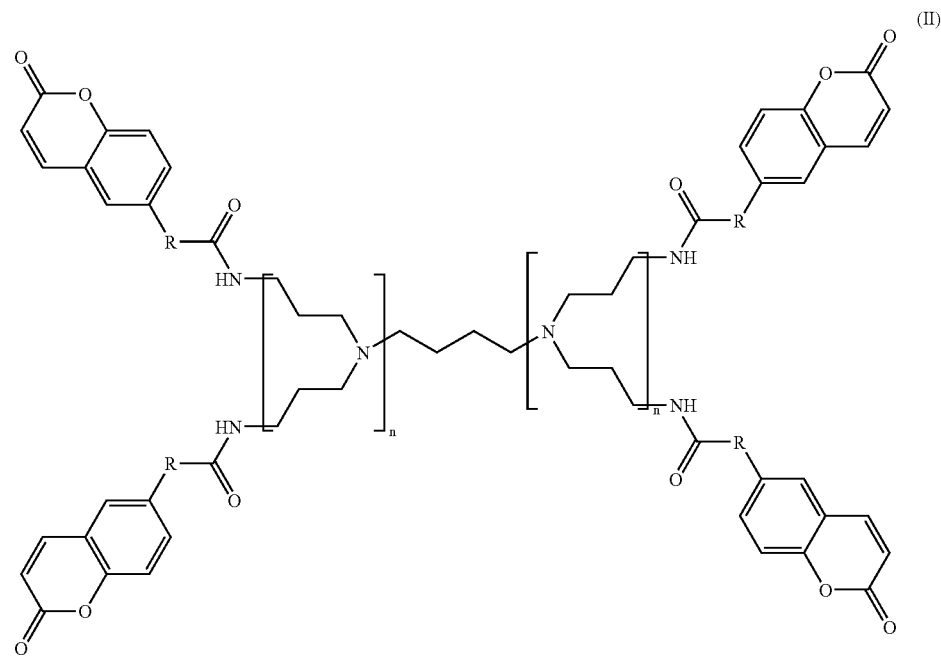

wherein n represents an integer of 10 or less and R represents a linkage group.

Here, in the general formulas (I) and (II), n is an integer of 1 to 10, preferably of 2 to 10, and further preferably of 3 to 8. In addition, R (a coupling group) in the general formula (2) includes, for instance, an alkenyl group with $C_1$ to $C_{10}$ and an alkynyl group with $C_2$ to $C_{10}$, but is not particularly limited so far as being a coupling group used for the dendrimer.

(8) Another invention according to the present application is "the method of producing a molecular device according to the item (7), wherein R in the general formula (II) is an alkenyl group with $C_1$ to $C_{10}$ or an alkynyl group with $C_2$ to $C_{10}$".

(9) Another invention according to the present application is "the method of producing a molecular device according to the item (7) or (8), wherein each n in the general formulas (I) and (II) is an integer of 2 to 10".

(10) Another invention according to the present application is "a molecular structure (a nano-particle) having a shell structure made by crosslinking the bonding residues of the molecular structure which has a higher atomic density in the periphery than in the interior and has the bonding residues in the periphery, into a shell".

(11) Another invention according to the present application is "a molecular device including the molecular structure having the shell structure according to the item (10)".

(12) Another invention according to the present application is "a method of producing a molecular device including: the use of a molecular structure having a plurality of bonding residues in the molecule, and a sensitizer; and the step of joining the bonding residues of the molecular structure by an energy imparting step of imparting energy to the sensitizer, to obtain the molecular structure having a shell structure". The energy imparted to the sensitizer propagates to the molecular structure. The energy having propagated to the molecular structure is used for joining the bonding residues. Here, "plurality" for the number of bonding residues means 2 or greater, and though varying with the structure of the molecular structure, the number of bonding residues is normally 4 or greater but 1,000 or less, preferably 8 or greater but 512 or less, and further preferably 16 or greater but 255 or less (hereafter, the same). The molecular structure obtained in such a step includes a functional nano-particle having a shell structure, and a molecular device comprising the functional nano-particles has various functions according to the properties of the various nano-particles.

(13) Another invention according to the present application is "a method of producing a molecular device including: the use of a molecular structure having a plurality of bonding residues in the molecule, and a sensitizer; an energy imparting step of imparting energy to the sensitizer; one or both stages of an energy transfer process of transferring the energy to the bonding residues from the energy-imparted sensitizer, and an electron-imparting process of transferring electrons to the bonding residues from the energy-imparted sensitizer; and a step of obtaining the molecular structure having a shell structure by using the energy transfer process or the electron-imparting process as a driving force for the chemical bonding reaction of the bonding residues". The molecular structure obtained in such steps includes a functional nano-particle having the shell structure, and a molecular device comprising the functional nano-particles has various functions according to the properties of the various nano-particles.

(14) Another invention according to the present application is "a method of producing a molecular device including: the use of a molecular structure having a plurality of bonding residues in the molecule, a sensitizer and a crosslinking agent containing a plurality of bonding residues; and the step of crosslinking the bonding residues in the molecule of the molecular structure with the crosslinking agent by using an energy imparting step of imparting energy to the sensitizer, to obtain a molecular aggregate which three-dimensionally combines a plurality of molecular structures". The molecular assembly obtained through such a step includes a nano-wire. One example of the nano-wire includes one having the molecular structures regularly disposed. Each molecular structure functions as a molecular device having various functions such as an optical memory effect. In addition, a molecular aggregate (or a molecular device) having various functions can be produced by combining the molecular structures one-dimensionally, two-dimensionally and three-dimensionally one after another into a linear shape, a grid shape or a radical shape. The position where the molecular structure is combined, can be controlled by controlling the position of the bonding residue in the molecular structure, which leads to a control of the growing direction in the molecular aggregate formed by a sequential coupling of the molecular structure and the extension. In addition, spacings among the molecular structures constituting the molecular aggregate, can be controlled by controlling the length of a crosslinking agent. Here, the number of bonding residues existing inside the crosslinking agent is not particularly limited so far as being 2 or more, but is preferably 2 or more but 10 or less, and further preferably 2 or more but 4 or less (hereafter, the same). In addition, if the crosslinking agent of a medium shows a liquid crystal property, it is possible to impart directionality to a nano-wire by applying an external field such as an electric field and a magnetic field.

(15) Another invention according to the present application is "a method of producing a molecular device including: the use of a molecular structure having a plurality of bonding residues in the molecule, a sensitizer, and a crosslinking agent containing a plurality of bonding residues; the energy imparting step of imparting energy to the sensitizer; one or both of an energy transfer process and an electron transfer process, which are stages including energy transfer or electron transfer from the energy-imparted sensitizer to one or both of the bonding residues of the structure and the bonding residues of the crosslinking agent; and the step of crosslinking the bonding residues in the molecule of the molecular structure with the crosslinking agent by the energy transfer process or the electron-imparting stage, to obtain a molecular aggregate having a plurality of molecular structures three-dimensionally combined through the crosslinking agent". The molecular aggregate obtained through such steps includes a nano-wire, for instance. One example of the nano-wire includes one having the molecular structures regularly disposed.

(16) Another invention according to the present application is "the method of producing a molecular device according to any one of the items (12) to (15), wherein the energy imparted to the sensitizer in the energy imparting step is an energy originating in any one of an electron, an ion and an electromagnetic wave, or a combination thereof".

(17) Another invention according to the present application is "the method of producing a molecular device according to any one of the items (12) to (15), wherein the energy imparted to the sensitizer in the energy imparting step is a light energy due to an ultra-violet ray, a visible ray and an infrared ray".

(18) Another invention according to the present application is "the method of producing a molecular device according to any one of the items (12) to (15), characterized in that the energy imparted to the sensitizer in the energy imparting step is a light energy due to an ultra-violet ray, a visible ray and an infrared ray; and that the energy transfers from the energy-imparted sensitizer to the bonding residues through an energy transfer process".

(19) Another invention according to the present application is "The method of producing a molecular device according to the item (18), wherein the energy imparted to the sensitizer in the energy imparting step is a light energy due to an ultra-violet ray, a visible ray and an infrared ray, and the energy transfer in the energy transfer process is a triplet energy transfer process".

(20) Another invention according to the present application is "the method of producing a molecular device according to any one of the items (12) to (19), wherein the bonding residue is an optically bonding residue".

(21) Another invention according to the present application is "the method of producing a molecular device according to any one of the items (12) to (19), wherein the bonding residue has at least one of one or both of a double bond and a triple bond".

(22) Another invention according to the present application is "the method of producing a molecular device according to any one of the items (12) to (19), wherein the bonding residue is one of a cinnamic acid group, an α-cyano cinnamic acid group, a coumarin group, a chalcone group, a cinnamylidene acetate group, a p-phenylene diacrylate group, an acetylene group, a diacetylene group, a diphenyl acetylene group and an anthracene group".

(23) Another invention according to the present application is "a method of producing a molecular device including: the use of a molecular structure having a higher atomic density in the periphery than in the interior and having bonding residues in the periphery, and a photosensitizer molecule that is included inside the molecular structure, or is covalently bonded, ionically bonded, coordinately bonded, metallically bonded or hydrogen bonded with the molecular structure; and a shell-forming step of joining the bonding residues by photoirradiation, to obtain the molecular structure having the shell structure".

(24) Another invention according to the present application is "the method of producing a molecular device according to the item (23), characterized in that the molecular structure is constituted by a skeleton portion having a skeleton structure and a terminal portion which is arranged in the outer shell of the skeleton portion, has a higher atomic density than that of the skeleton portion, and has a plurality of bonding residues; and that in the shell-forming step, the bonding residues in the terminal portion of the molecular structure are combined by irradiating the photosensitizer molecule with light".

(25) Another invention according to the present application is "the method of producing a molecular device according to the item (23), characterized in that the plurality of bonding residues existing in the terminal portion are combined to obtain the molecular structure having the shell structure".

(26) Another invention according to the present application is "the method of producing a molecular device according to the item (23), characterized in that the method further includes the use of the molecule of a crosslinking agent, makes the molecule of the crosslinking agent crosslink with the bonding residues, and three-dimensionally combines a plurality of molecular structures through the crosslinkable molecule".

(27) Another invention according to the present application is "the method of producing a molecular device according to any one of the items (23) to (26), wherein the bonding residue is an optically bonding residue".

(28) Another invention according to the present application is "the method of producing a molecular device according to any one of the items (23) to (26), wherein the bonding residue has at least one of one or both of a double bond and a triple bond".

(29) Another invention according to the present application is "the method of producing a molecular device according to any one of the items (23) to (26), wherein the bonding residue is any one of a cinnamic acid group, an α-cyano cinnamic acid group, a coumarin group, a chalcone group, a cinnamylidene acetate group, a p-phenylene diacrylate group, an acetylene group, a diacetylene group, a diphenyl acetylene group and an anthracene group".

(30) Another invention according to the present application is "the method of producing a molecular device according to any one of the items (12) to (29), wherein the molecular structure is a dendrimer".

(31) Another invention according to the present application is "the method of producing a molecular device according to the item (30), wherein the dendrimer is expressed by the following formula (I) or (II)":

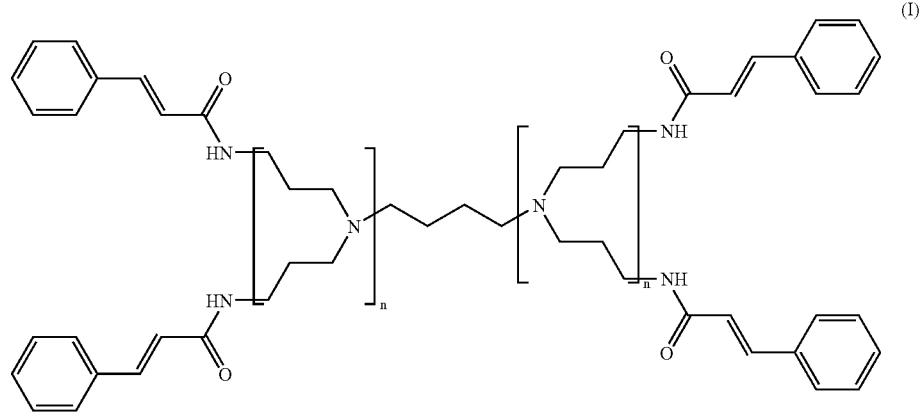

wherein n represents an integer of 10 or less, or

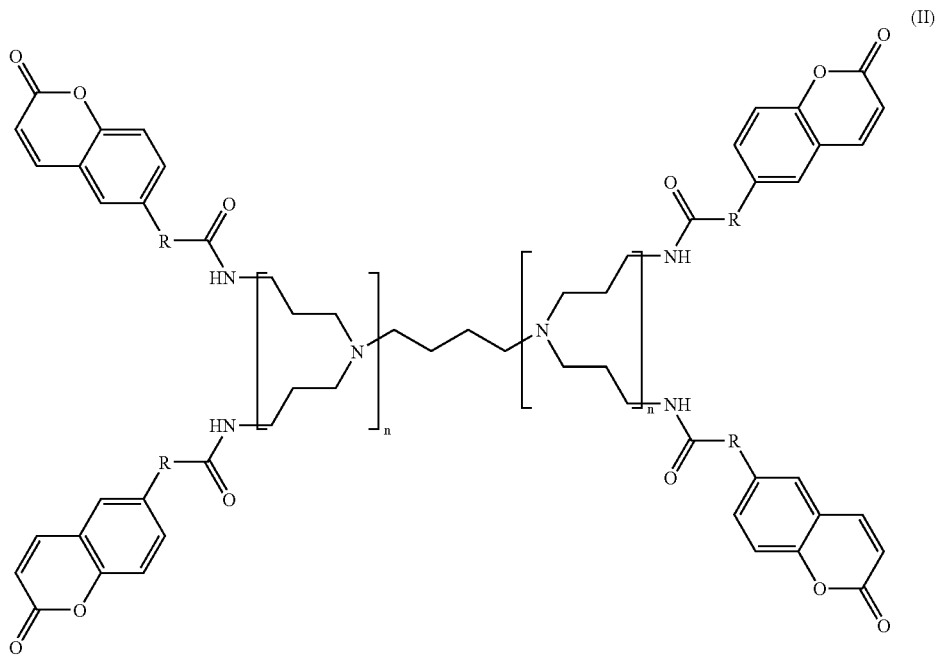

wherein n represents an integer of 10 or less and R represents a linkage group.

Here, in the general formulas (I) and (II), n is an integer of 1 to 10, preferably of 2 to 10, and further preferably of 3 to 8. In addition, R (a coupling group) in the general formula (II) includes, for instance, an alkenyl group with $C_1$ to $C_{10}$ and an alkynyl group with $C_2$ to $C_{10}$, but is not particularly limited so far as being a coupling group used for the dendrimer.

(32) Another invention according to the present application is "the method of producing a molecular device according to the item (31), wherein R in the general formula (II) is an alkenyl group with $C_1$ to $C_{10}$ or an alkynyl group with $C_2$ to $C_{10}$".

(33) Another invention according to the present application is "the method of producing a molecular device according to the item (31) or (32), wherein each n in the general formulas (I) and (II) is an integer of 2 to 10".

(34) Another invention according to the present application is "a molecular structure having a shell structure obtained by: using a molecular structure constituted by a skeleton portion having a skeleton structure, and a terminal portion which is arranged in the outer shell of the skeleton portion, has a higher atomic density than that of the skeleton portion and has a plurality of bonding residues, and a photosensitizer molecule included inside the molecular structure; and joining the bonding residues in the terminal portion by taking advantage of the spectral sensitization of the photosensitizer molecule irradiated with light".

(35) Another invention according to the present application is "a molecular aggregate obtained by: using a molecular structure constituted by a skeleton portion having a skeleton structure, and a terminal portion which is arranged in the outer shell of the skeleton portion, has a higher atomic density than that of the skeleton portion and has a plurality of bonding residues, a photosensitizing molecule contained inside the molecular structure, and the molecule of a crosslinking agent; and crosslinking the bonding residues with the molecule of the crosslinking agent through irradiating the photosensitizer molecule with light to combine a plurality of molecular structures".

(36) Another invention according to the present application is "a molecular device including the molecular structure having the shell structure according to the item (34), or the molecular aggregate according to the item (35)".

BEST MODE FOR CARRYING OUT THE INVENTION

Figure 1:
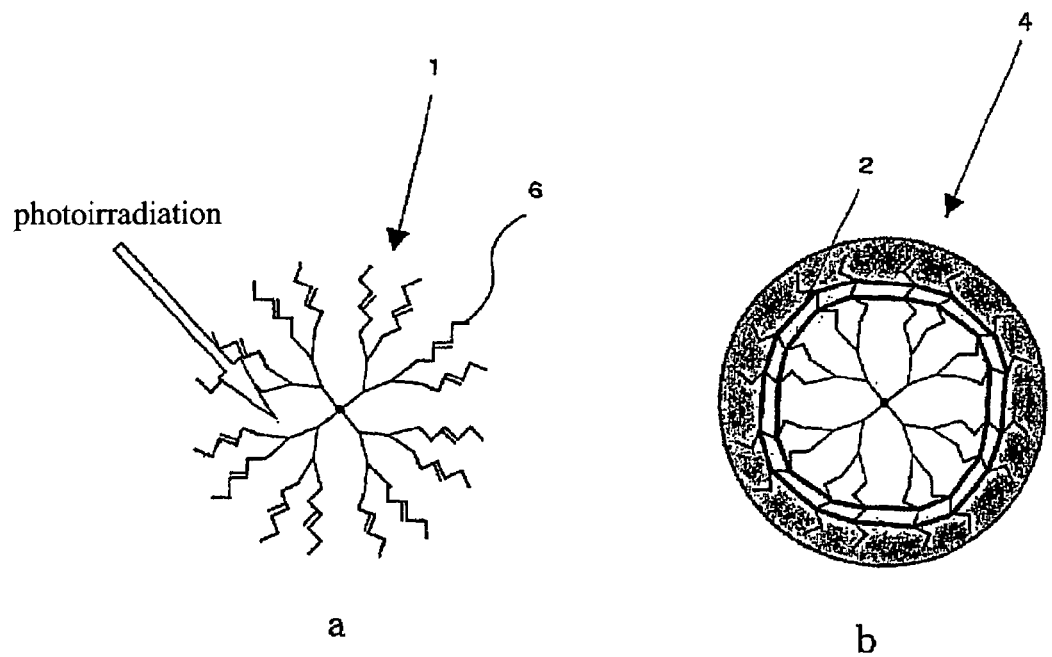
FIG. 1 is a conceptual diagram of a molecular structure (a nano-particle) having a shell structure.

A method of producing a molecular structure, a molecular aggregate and a molecular device according to the present invention will be now described in detail below.

A method of producing a molecular device according to the present invention uses a molecular structure which has a higher atomic density in the periphery than in the interior and has a bonding residue in the periphery. According to one example according to the present invention, a molecular structure or a molecular aggregate is produced by crosslinking the bonding residue existing in the periphery of the molecular structure, within the molecular structure or between the molecular structures.

In another example according to the present invention, an energy is imparted to a solution or a solid containing a molecular structure and a sensitizer through the light having wavelengths absorbed by the above described sensitizer, or the like. The solution or the solid may contain a binding resin (a binder) and other secondary materials. In the present invention, a molecular structure having a shell structure or a molecular aggregate having the molecular structures three-dimensionally combined is produced by using a phenomenon that light energy is absorbed in a sensitizer; the energy absorbed by the sensitizer transmits to a molecular structure such as a dendrimer; alternatively an electron, an ion or a radical migrates; and the energy causes a bonding reaction or a crosslinking reaction of the bonding residue existing in the molecular structure.

Each molecular structure preferably functions as a molecular element having various functions such as an optical memory effect. Then, a molecular aggregate (or a molecular device) having various functions can be produced by one-dimensionally, two-dimensionally and three-dimensionally combining the molecular structures one after another into a linear shape, a grid shape or a radical shape. The position where the molecular structure is combined, can be controlled by controlling the position of the bonding residue in the molecular structure, which leads to a control of the growing direction in the molecular aggregate formed by a sequential coupling of the molecular structure and the extension. In addition, spacings among the molecular structures composing the molecular aggregate can be controlled by controlling the length of a crosslinking agent.

Here, a molecular structure means a molecule in which a plurality of parts having different functions exist in different portions of one molecule such as a residue part and a central part. The molecular structure includes the one constituted by a skeleton portion having a skeleton structure, and a terminal portion which is arranged in the outer shell (outside) of the skeleton portion, has a higher atomic density than that of the skeleton portion, and has bonding residues. The molecular structure preferably has a plurality of (two or more) bonding residues. The bonding residue is preferably an optically bonding residue. The molecular structure is preferably a dendrimer. The dendrimer is preferably one shown in the above described general formula (I) or in the above described general formula (II). Here, n in the general formulas (I) and (II) is an integer of 1 to 10, preferably of 2 to 10, and further preferably of 3 to 8. In addition, R in the general formula (II) includes an alkenyl group with $C_1$ to $C_{10}$ and an alkynyl group with $C_2$ to $C_{10}$, but is not particularly limited so far as being a coupling group used for the dendrimer.

The molecular structure is preferably a molecule which can contain a sensitizer, or a molecule which is covalently bonded, ionically bonded, coordinately bonded, metallically bonded or hydrogen bonded with a sensitizer, and particularly preferably a dendrimer (a hyper-branched polymer) having an optical functionality and an electronic functionality, but is not limited in particular so far as being a compound having a bonding residue. The molecule of the dendrimer has a nanometric space in itself, and has an uniqueness capable of including a foreign molecule or a foreign atom in the space. Details on encapsulation phenomenon of the dendrimer are described in Science, 266, 1226 (1994) by J. Jansen, E. Berg and E. Meijer; and in Nature, 389 and 368 (1997), by A. Cooper, J. Londono, G. Wignall, J. McClain, E. Samulski, J. Lin, A. Dobrynin, M. Rubinstein, A. Burke, J. Frechet and J. DeSimone; which are both scientific magazines.

A bonding residue (an photocrosslinkable residue) in a molecular structure includes (a) an aliphatic residue having an unsaturated double bond, such as a vinyl group, an acrylate group and a methacrylate group, (b) an aromatic residue having an unsaturated double bond, such as a cinnamic acid group, an α-cyano cinnamic acid group, a coumarin group, a chalcone group, a cinnamylidene acetate group, a p-phenylene diacrylate group, a distyrylpyrazine group and an anthracene group, (c) an aliphatic residue having an unsaturated triple bond, such as an acetylene group and a diacetylene group, and (d) an aromatic residue having an unsaturated triple bond, such as a diphenylacetylene group, a phenyl azide group and a dypyridyl diacetylene group. In addition, the derivative materials thereof are also acceptable. The residues in (a) require a radical photopolymerization initiator in order to show a radical polymerization reaction. On the other hand, the photocrosslinkable residues in (b) to (d) do not require such a photopolymerization initiator as is required in the case of (a), because they show a photoaddition reaction according to the Woodward-Hoffmann's law, such as a [2π-2π] photodimerization reaction. Details on these photosensitive residues are described in "Photosensitive Polymer" of Kodansha scientific (1977), by Nagamatsu Mototaro and Inui Hideo.

As for the irradiation light used when preparing a crosslinked body by the light, an x-ray, an electron beam, an ultra-violet ray, a visible ray or an infrared-ray (a heat ray) is used. Among them, the ultraviolet ray or the visible ray is particularly preferable. A usable light source includes an extra-high pressure mercury lamp, a low pressure mercury lamp, a xenon lamp, a mercury xenon lamp, a halogen lamp, a fluorescent lamp, a gas laser, a liquid laser, and a solid state laser. In addition, the surface plasmon radiation of the light emitted from these light sources may be used.

Figure 2:
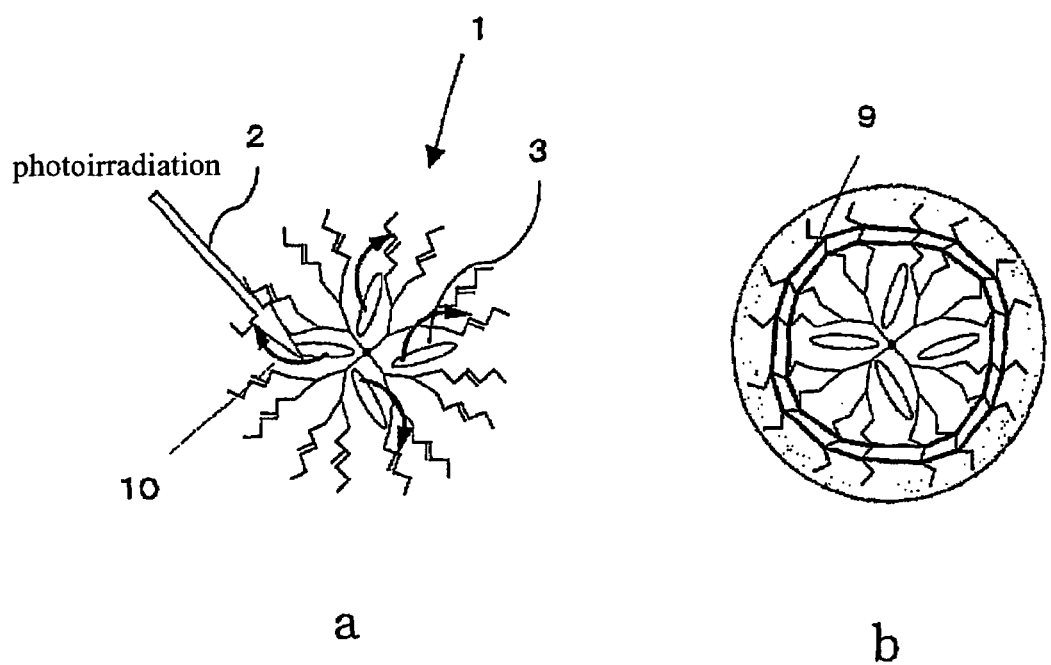
FIG. 2 is a conceptual diagram of a nano-particle according to the present invention.
Figure 4:
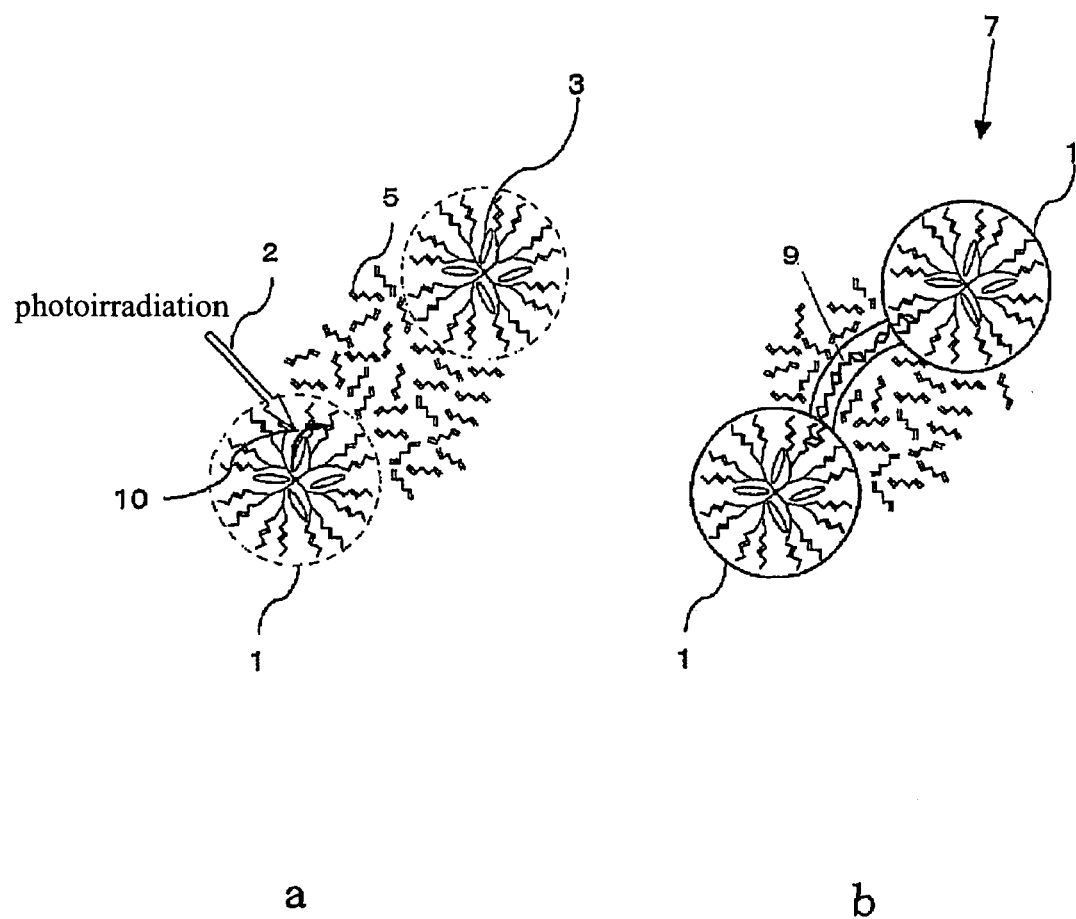
FIG. 4 is a conceptual diagram of a nano-wire according to the present invention.

In order to combine (crosslink) bonding residues mutually or molecular structures each other, the bonding residue may be directly excited to induce an intramolecular bonding or an intermolecular bonding, and intramolecular crosslinking and intermolecular crosslinking may be formed with the use of a crosslinking agent. In order to combine each molecular structure, a bonding residue (a photocrosslinkable residue) may be directly excited to induce an photocrosslinking reaction, but in order to more efficiently and more selectively cause coupling inside a nanometric region in the molecular structure and coupling between molecular structures, "spectrum sensitization" is preferably used. By thus using spectrum sensitization, as shown in FIG. 2 and FIG. 4, a nano-particle and nano-wire of the molecular structure becomes easily produced. In the preparation step, a sensitizer, so to speak, is preferably added which is a molecule capable of spectrally sensitizing a bonding residue (a photocrosslinkable residue) by using the uniqueness of a dendrimer molecule capable of including a foreign molecule or a foreign atom inside itself, as described above. The detail of the sensitizer is described in "Sensitizer", Kodansha scientific, (1987) by Tokumaru Katsuyuki and Okawara Makoto. The mechanism of spectrum sensitization includes a photoelectron transfer and a light energy transfer. The light energy transfer is broadly divided into two types according to a photoexcited state. One is a singlet energy transfer (Forster's type) based on a dipole-dipole interaction, and the other is a triplet energy transfer (Dexter's type) based on an electron exchange interaction. The detail of the light energy transfer is described in Modern Molecular Photochemistry, University Science Books (1991) by N. Turro. The transfer distance of the photoelectron transfer is about 0.4 to 2.0 nm, and the transfer distances of the singlet and triplet energy transfers are respectively about 1.0 to 10 nm and 0.3 to 1.0 nm. Among these spectrum sensitization mechanisms, in the present invention, the triplet energy transfer for spectrum sensitization in a nanometric region is preferably used to optically combine the optically and/or electronically functional molecular structures.

In the present specification, crosslinking means combining two or more molecular structures by using a crosslinking agent, and besides, combining bonding residues in the same molecular structure or between the molecular structures without using the crosslinking agent. In the present invention, a crosslinking agent means a molecular for joining the bonding residues in a molecular structure mutually. The crosslinking agent includes, for instance, butadiene, pentadiene and a hydrocarbon having the bonding residue in the molecular structure. The crosslinking agent combines molecular structures mutually while controlling the spacing, by controlling the length of itself, and provides a molecular aggregate having regularity.

In a method of producing a molecular device according to the present invention, a molecular structure or molecular aggregate having a shell structure described bellow may be obtained as an intermediate product.

The molecular structure having the shell structure (hereafter also called a "nano-particle") is produced, for instance, by crosslinking the bonding residues of a molecular structure which has a higher atomic density in the periphery than in the interior and has the bonding residues in the periphery, into the shell. More specifically, the molecular structure having the shell structure is a substance having the bonding residues existing in the periphery of the molecular structure combined and form a shell-like state. In particular, when the molecular structure has not so high a density, and a large intermolecular distance between the molecular structures, it mainly produces a nano-particle.

FIG. 1 shows a conceptual diagram of a nano-particle. FIG. 1(a) shows a molecular structure (a dendrimer) 1. When the molecular structure shown in FIG. 1(a) is irradiated with light, the bonding residue 6 inside the molecular structure is crosslinked (combined) to form crosslinking part shown in FIG. 1(b)-2. Thus, the nano-particle 4 is formed which is the molecular structure having the shell structure. The crosslinking reaction can be performed in a solvent such as dichloromethane, and may be performed in a solid phase as well.

One example of a nano-particle will be described with reference to FIG. 2. A molecular structure 1 such as a dendrimer has a sensitizer 3 in the periphery and the interior (FIG. 2(a)). The sensitizer absorbs energy by photoirradiation. The absorbed energy by the sensitizer is transferred to the molecular structure as shown by numeral 10. Then, in the molecular structure 1, bonding residues are mutually combined (crosslinked) by the transferred energy to form a crosslinking reaction part 9 (FIG. 2(b)). Thus, the crosslinking reaction part forms a shell and a consequent nanoparticle.

A molecular assembly having a plurality of molecular structures combined, (hereafter also called a nano-wire) is produced, for instance, by crosslinking the connective residues in a molecular structure which has a higher atomic density in the periphery than in the interior and has the connective residues in the periphery, and combining the connective residues of the adjacent molecular structures. The molecular structure according to the present invention has a plurality of bonding residues, for instance, inside the molecular. Then, when crosslinking proceeds, a plurality of molecular structures are radially assembled. In particular, when the molecular structure has a high density, and a small intermolecular distance between the molecular structures, it mainly produces a nano-wire.

Figure 3:
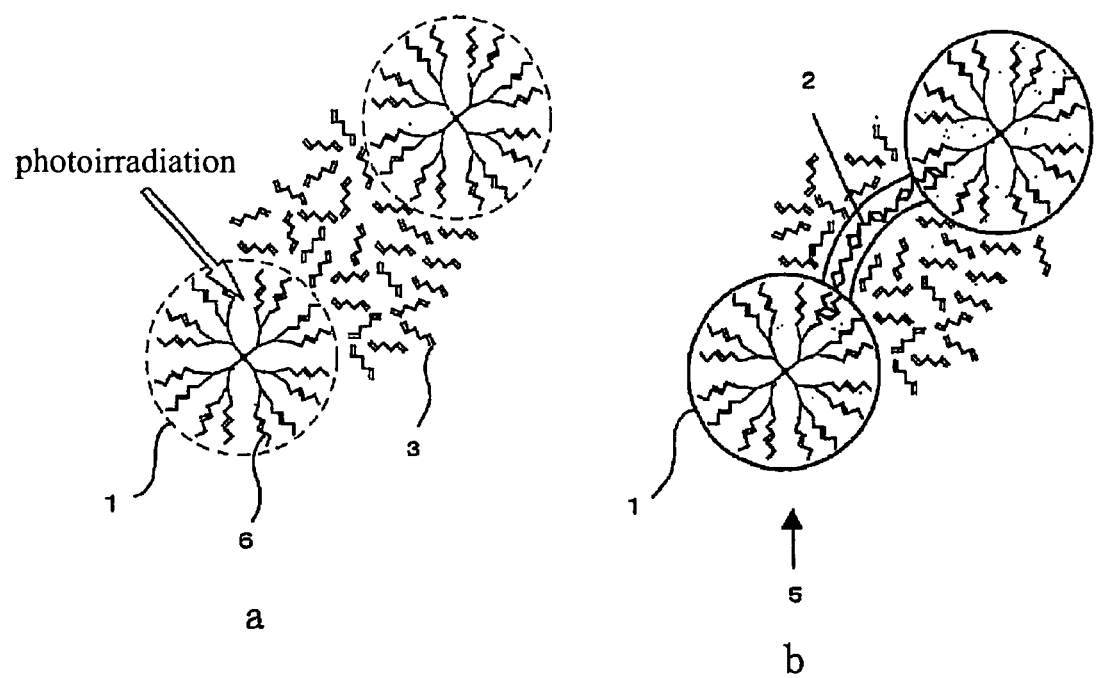
FIG. 3 is a conceptual diagram of a molecular aggregate (a nano-wire)

For reference, a conceptual diagram of a nano-wire is shown in FIG. 3. As for one example of producing a molecular aggregate, as shown in FIG. 3(a), the molecular structure 1 having the bonding residues 6 in the periphery is irradiated with light. Then, as shown in FIG. 3(b), a crosslinkable residue in the molecular structure 1 and a crosslinking agent 3 are crosslinked to obtain a molecular aggregate 5.

In addition, when the crosslinking proceeds by an added crosslinking agent, the bonding residue in the molecular structure causes a crosslinking reaction with the crosslinking agent. In the above step, by controlling the length of the crosslinking agent, the molecular structures can assemble keeping distances among the molecular structures controlled, to form a molecular aggregate.

A molecular aggregate according to the present invention, (hereafter also called a nano-wire) is produced, for instance, by crosslinking the bonding residues in a molecular structure which has a higher atomic density in the periphery than in the interior and has the bonding residues in the periphery, and joining the bonding residues of the adjacent molecular structures. Another example of a nano-wire is described with reference to FIG. 4. As shown in FIG. 4(a), the molecular structure 1 having bonding residues in the periphery and the sensitizer 3 are irradiated with light. The sensitizer absorbs energy due to photoirradiation. The absorbed energy by the sensitizer is transferred to the molecular structure as shown by numeral 10. Then, as shown in FIG. 4(b), the crosslinkable residue and the crosslinking agent 5 in the molecular structure 1 are crosslinked to form the crosslinking reaction part 9 and provide the molecular aggregate 7 (FIG. 4(b)).

In addition, when the crosslinking proceeds by addition of a crosslinking agent, the bonding residue in the molecular structure causes a crosslinking reaction with the crosslinking agent, and the molecular structures can assemble keeping distances among the molecular structures controlled, to form a molecular aggregate as well.

A molecule device includes, for instance, devices with the use of the above described nano-particle or nano-wire. A molecular structure has various functions. Accordingly, by controlling the aggregated form of the molecular structures in a molecule-level or a nano-level, a molecular device can be obtained. For instance, by crosslinking the bonding residues in the molecular structures while controlling the positions, the three-dimensional structure of a molecular aggregate can be controlled.

Figure 5:
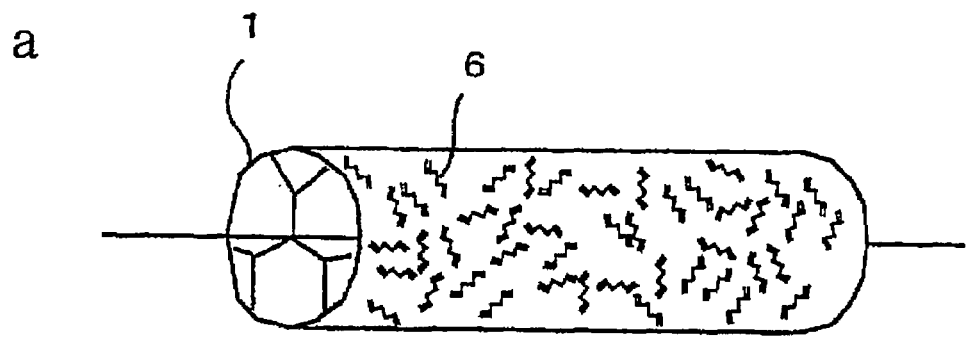
FIG. 5 is a conceptual diagram of a photoconductive nano-wire by a rod-shaped dendrimer.
Figure 5:
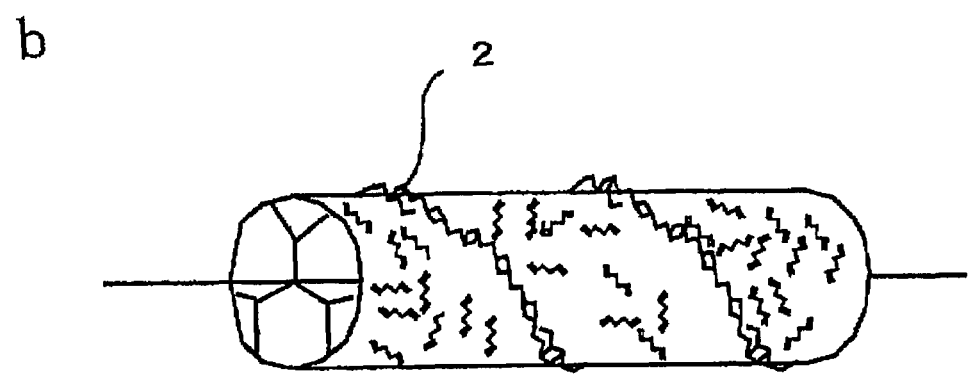

FIG. 5 shows a conceptual diagram of a photoconductive nano-wire using a rod-shaped dendrimer, which is one example of a molecular device according to the present invention.

FIG. 5(a) shows a rod-shaped dendrimer molecule of which the circumference is modified with bonding residues. When a solution containing the dendrimer is irradiated with light, the bonding residues in the dendrimer are combined, and a photoconductive nano-wire which is a molecular device as shown in FIG. 5(b), can be obtained. The photoconductive nano-wire has approximately equal formation rates of a free electron and a positive hole, so that it behaves like an intrinsic semiconductor. More specifically, by using such a molecular device, a semiconductor element having the shape controlled in a nanometric level can be obtained. The really obtained photoconductive nano-wire had the electron mobility of about 1 $cm^2/V$ in the axial direction and about 0.001 $cm^2/V$ in the radial direction.

Furthermore, when the void of the photoconductive nano-wire was doped with iodine, the electroconductivity of the photoconductive nano-wire was drastically improved.

Figure 6:
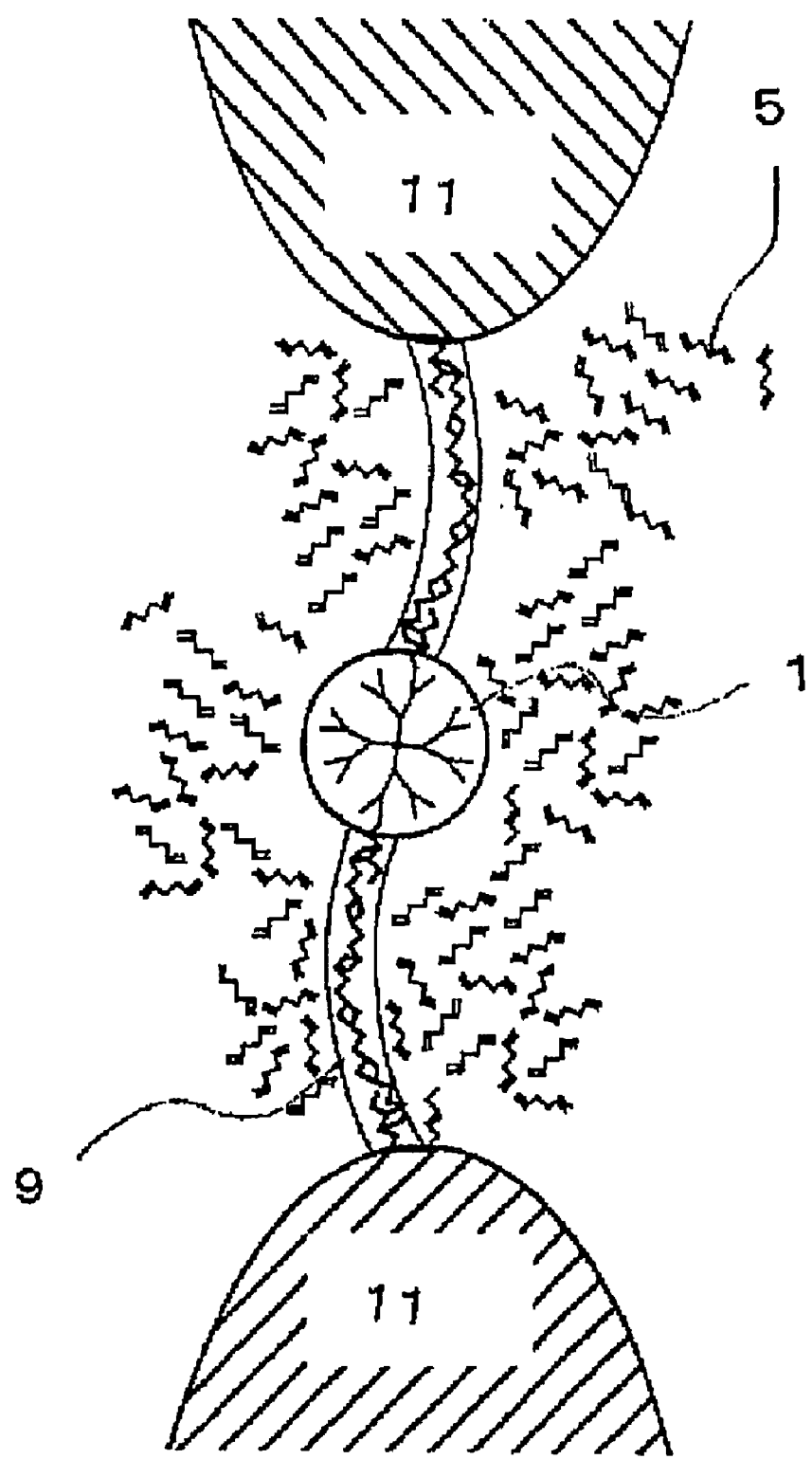
FIG. 6 is a conceptual diagram showing one example of a single electron transistor (SET)

A molecular structure has various functions. Accordingly, for instance, by combining such molecular structures one after another toward a preferable direction through a crosslinking agent, a molecular device can be obtained. The crosslinked part can be an information transfer path when the molecular structure having functionality transfers information such as an electric signal. By such a method, a molecular device can be obtained which functions as an information transfer system as if a neuron extends an axon to other neurons. In addition, when a method of producing the molecular device is applied between electrodes, molecular structures are combined, and the molecular device capable of transmitting information can be obtained. By using the molecular device, a functional product can be obtained which uses the molecular device consisting of combined molecular elements (molecular structures) having functionality. FIG. 6 is a conceptual diagram showing one example of a single electron transistor (SET) of a molecular device which can be produced with such a production method. In FIG. 6, numeric 1 expresses a molecular structure which can function as a molecular element, numeric 5 expresses a crosslinking agent, numeric 9 expresses a crosslinking reaction part, and numeric 11 expresses an electrode. A SET shown in FIG. 6 was produced as described below. At first, an electrode 11 having a spacing of about 50 nm was prepared. The spacing of the electrode 11 can be controlled to about 10 nm to 1 μm. Then, a dendrimer having bonding residues at both poles (in opposed positions), and a solution containing a sensitizer and a crosslinking agent were prepared so as to combine the electrodes. Then, the solution containing the dendrimer was irradiated with light. Then, a molecular device (SET) as shown in FIG. 6 could be obtained. When voltage was applied on the molecular device, a phenomenon showing a stepped current-voltage characteristic (a Coulomb blockade phenomenon) was observed. From the result, it was found that the crosslinking agents combined mutually by photoirradiation functions as a tunnel layer.

Figure 7:
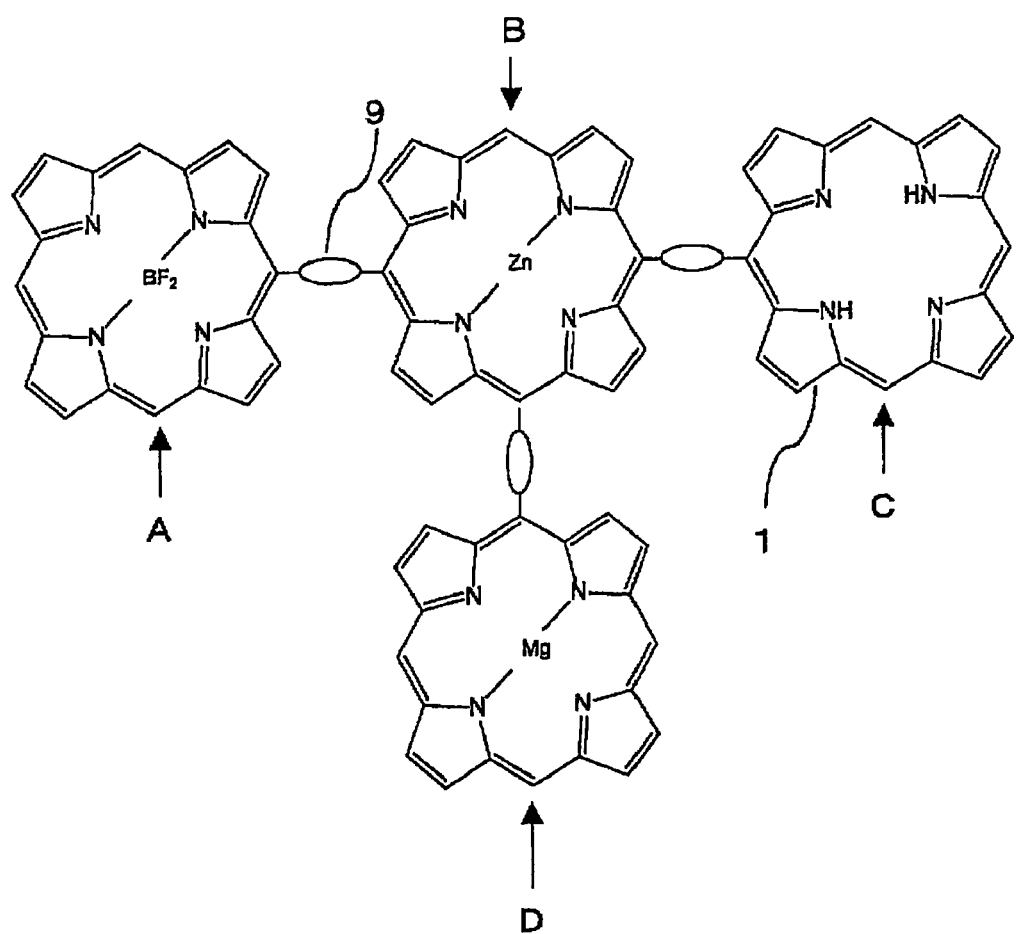
FIG. 7 is a conceptual diagram showing one example of a T-type optoelectronic device (TOED)

FIG. 7 is a conceptual diagram showing one example of a T-type optoelectronic element (TOED) which is another molecular device according to the present invention.

One example of methods of producing TOED is now described below. At first, a substrate made of mica was prepared. The substrate may be an insulator such as gold, copper, platinum and mica. Subsequently, the substrate was immersed into a solution containing four types of molecular structures A, B, C and D, and a sensitizer. In the above solution, a crosslinking agent may be contained. The molecular structure A has such a bonding residue in the first position as to be combined with a certain bonding residue in the molecular structure B. The molecular structure A may have such a bonding residue in the tenth position as to be combined with a certain bonding residue in the molecular structure C. (In this case, the obtained molecular device is not a TOED but a continuum of a T-type optoelectronics.) The molecular structure B has each bonding residue in the first position, the fifth position and the tenth position as to be combined with each certain bonding residue respectively in the molecular structures C, D and A. The molecular structure B may have such a bonding residue in the 15th position as to be combined with a certain bonding residue in the molecular structure D. (In this case, the obtained molecular device is not a TOED but a continuum of a T-type optoelectronics.)

When the solution was irradiated with light, a molecular device was formed on the substrate.

When an optical signal was input in the molecular structure A out of the molecular devices, an output was observed from the molecular structure B after 30 picoseconds.

On the other hand, when the molecular structure D was oxidized and then an optical signal was input in the molecular structure A, the output was not obtained from the molecular structure B.

In addition, by using a molecular device according to the present invention, a molecular integrated circuit, for instance, described in Japanese Patent Laid-Open No. 2001-44413, can be manufactured. The molecular integrated circuit with the use of the molecular device according to the present invention, can be used as a NAND circuit, a NOR circuit, an inverter circuit, a random access memory cell and a read only memory cell, as in the case of a molecular integrated circuit described in Japanese Patent Laid-Open No. 2001-44413. In the present invention, because a molecular device can be constructed by using a photosensitization reaction, molecular devices can be more precisely and speedily produced.

PRODUCTION EXAMPLE 1

Method of Synthesizing Dendrimer Having Cinnamic Acid Amide Residue in Terminal

Into a dichloromethane solution of a poly(propyleneimine)dendrimer (1.0 g, 3.2 mmol, made by Aldrich Corporation) of the first generation (n=1 in FIG. 8) containing a catalytic quantity of triethylamine, a solution of trans-cinnamyl chloride (0.63 g, 3.7 mmol, made by Aldrich Corporation) was dropped, and the resultant solution was stirred at 0° C. for one hour and then at room temperature for 40 hours. This reaction liquid was diluted with dichloromethane, was cleaned sequentially with ion-exchange water, an aqueous solution of sodium carbonate and an aqueous solution of sodium chloride, and was dried with magnesium sulfate. After filtration, dichloromethane was removed by an evaporator. The crude product was dialyzed and reprecipitated repetitively for three times, and was dried under a reduced pressure. Then, a white solid was obtained.

Each poly(propyleneimine)dendrimer of the third generation and the fifth generation (respectively n=3 and 5 in FIG. 8) was also synthesized and refined with a similar method to the above described method.

Various physical properties of thus synthesized dendrimer are shown in Table 1 and Table 2.

TABLE 1

A plurality of physical properties of synthesized dendrimer
Results of measurement on weight average molecular weight and
molecular weight distribution by size exclusion chromatography

| Dendrimer | Weight average molecular weight | Molecular weight distribution | Calculated value |
|---|---|---|---|
| First generation | 905 | 1.02 | 837 |
| Third generation | 4103 | 1.01 | 3768 |
| Fifth generation | 16084 | 1.02 | 15497 |

TABLE 2

Results of measurement of melting point by differential scanning calorimetry

| Dendrimer | First generation | Third generation | Fifth generation |
|---|---|---|---|
| Melting point (° C.) | 150 | 103 | 93 |

TABLE 3

Results of measurement of absorption spectrum after photoirradiation
in dilute solution of propylene imine dendrimer

| | Quantity of exposure energy (J/cm$^2$) | Trans isomer (%) | Cis isomer (%) | Associated body (%) |
|---|---|---|---|---|
| First generation | 0.4 | 86 | 11 | 3 |
| | 2.0 | 56 | 39 | 5 |
| | 10 | 40 | 48 | 12 |
| | 20 | 30 | 53 | 17 |
| | 30 | 21 | 59 | 20 |
| Third generation | 0.4 | 87 | 9 | 4 |
| | 2.0 | 62 | 25 | 13 |
| | 10 | 40 | 34 | 26 |
| | 20 | 24 | 39 | 37 |
| | 30 | 19 | 40 | 41 |
| Fifth generation | 0.4 | 83 | 10 | 7 |
| | 2.0 | 66 | 17 | 17 |
| | 10 | 46 | 21 | 33 |
| | 20 | 34 | 24 | 42 |
| | 30 | 24 | 26 | 50 |

EXAMPLE 1

Production of Nano-Particle

EXAMPLE 1-1

Figure 8:
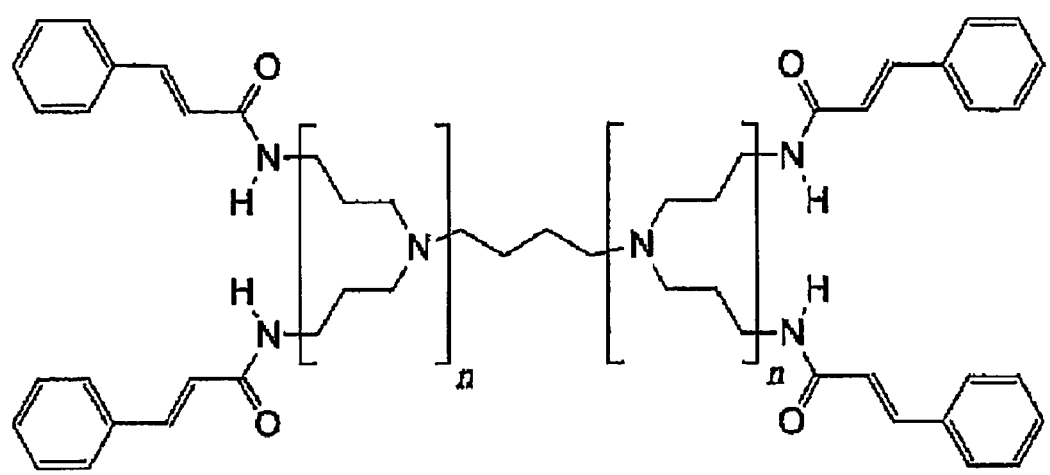
FIG. 8 shows one example of a dendrimer.

With the use of polypropylene imine dendrimer of the first generation (n=1) having residues of cinnamamide in the periphery of the molecular as shown in FIG. 8, the following experiment was carried out. A plurality of dichloromethane dilute solutions containing 3.0×10-5 (mol/L) of the dendrimer having cinnamamide by molar unit of cinnamamide in the dendrimer were prepared and were put in quartz cells having a dimension of 1.0 cm per side. The light having a wavelength of 313 nm which was taken out from a mercury xenon lamp having an output of 200 W, irradiated the previously prepared solution. With the photoirradiation, the absorption bands around 280 nm originated in the residue of cinnamamide decreased. The absorption spectrum after the photoirradiation was measured, and the abundance ratio of each trans isomer, cis isomer and associated body of the cinnamamide residue was calculated. The result is shown in Table 3. Here, the associated body means a product in which the cinnamamide residues are mutually combined.

EXAMPLE 1-2

As in the Example 1-1 except that the polypropylene imine dendrimer of the third generation (n=3 in FIG. 8) was employed, an experiment was carried out. The result is shown in Table 3.

EXAMPLE 1-3

As in the Example 1-1 except that the polypropylene imine dendrimer of the fifth generation (n=5 in FIG. 8) was employed, an experiment was carried out. The result is shown in Table 3.

From the Table 3, it was found that in the bonding dendrimer molecule associated with the present invention, as the quantity of exposure energy in a dilute solution increases, the ratio of the trans isomer of the cinnamamide residue decreases; whereas the ratio of the cis isomer and the associated body increases. It was found that particularly the increasing ratio of the associated body strongly depends on the generation of the dendrimer molecule, and the dendrimer of the fifth generation effectively forms the associated body. A fully irradiated solution with light was subjected to gel permeation chromatography, and the retention times before and after the photoirradiation were measured to prove that they were not changed. It means that the molecular weight of the dendrimer was maintained before and after the photoirradiation. Accordingly, in the solution of the dilute concentration, a coupling reaction occurred not between molecules but inside the dendrimer molecule, which means that a nano-particle was produced in the dilute solution. The nano-particle is considered to form in such a manner that the cinnamyl residues in a polypropylene imine dendrimer were photoexcited, and sequentially caused dimerization (intramolecular coupling) with the adjacent cinnamyl residues. Because with the increase of the generation of a polypropylene imine dendrimer, the density of the cinnamyl residue increases, the ratio of the associated body consisting of mutually combined cinnamyl residues also increases with the increase of the generation of the dendrimer.

COMPARATIVE EXAMPLE 1

Instead of the bonding dendrimer used in the above described Example 1-1, cinnamamide was employed and the dilute solution was prepared. Then the solution was irradiated with light as in the Example 1. The result is shown in Table 4.

TABLE 4

Results of measurement of absorption spectrum after photoirradiation
in a dilute cinnamamide solution

| | Quantity of exposure energy (J/cm$^2$) | Trans isomer (%) | Cis isomer (%) | Associated body (%) |
|---|---|---|---|---|
| Cinnamamide | 0.4 | 82 | 16 | 2 |
| | 2.0 | 40 | 56 | 4 |

TABLE 4-continued

Results of measurement of absorption spectrum after photoirradiation in a dilute cinnamamide solution

| Quantity of exposure energy (J/cm$^2$) | Trans isomer (%) | Cis isomer (%) | Associated body (%) |
|---|---|---|---|
| 10 | 23 | 73 | 4 |
| 20 | 23 | 72 | 5 |
| 30 | 21 | 74 | 5 |

The comparison of the above described Table 3 with the Table 4 makes it clear that the formation rate of the associated body of cinnamamide is greatly different from that of the crosslinkable dendrimer, and is extremely low.

EXAMPLE 2

Production of Nano-Particle in Solid Layer

EXAMPLE 2-1

With the use of a polypropylene imine dendrimer of the first generation (n=1), the following experiment was carried out. So as to have the ratio of a cinnamamide unit to a methyl methacrylate monomer unit in a dendrimer controlled to 1:10, a solution was prepared which contains the crosslinkable dendrimer diluted and dispersed in poly(methyl methacrylate). Each aliquot of the dichloromethane solution thus prepared was applied onto a glass substrate with a spin coating method. The solution was dried and solidified, then the light having the wavelength of 313 nm was taken out from a mercury xenon lamp having the output of 200 W, and the glass substrate was irradiated with it. With the photoirradiation, the absorption bands around 280 nm originated in the residue of cinnamamide was decreased. The absorption spectrum after the photoirradiation was measured, and the abundance ratio of each trans isomer, cis isomer and associated body of the cinnamamide residue was calculated. The result is shown in Table 5.

EXAMPLE 2-2

As in the Example 2-1 except that the polypropylene imine dendrimer of the third generation (n=3 in FIG. 8) was employed, an experiment was carried out. The result is shown in Table 5.

EXAMPLE 2-3

As in the Example 2-1 except that the polypropylene imine dendrimer of the fifth generation (n=5 in FIG. 8) was employed, an experiment was carried out. The result is shown in Table 5.

TABLE 5

Results of measurement of absorption spectrum after photoirradiation in solid layers of propylene imine dendrimer

| | Quantity of exposure energy (J/cm$^2$) | Trans isomer (%) | Cis isomer (%) | Photocross-linked body (%) |
|---|---|---|---|---|
| First generation | 0.2 | 90 | 9 | 1 |
| | 1.0 | 72 | 21 | 7 |
| | 5.0 | 46 | 28 | 26 |
| | 9.0 | 34 | 29 | 37 |
| | 15 | 27 | 28 | 45 |
| Third generation | 0.2 | 89 | 7 | 4 |
| | 1.0 | 67 | 17 | 16 |
| | 5.0 | 36 | 29 | 35 |
| | 9.0 | 24 | 31 | 45 |
| | 15 | 16 | 32 | 52 |
| Fifth generation | 0.2 | 88 | 6 | 6 |
| | 1.0 | 57 | 20 | 23 |
| | 5.0 | 28 | 27 | 45 |
| | 9.0 | 18 | 27 | 55 |
| | 15 | 12 | 28 | 60 |

It was found from Table 5 that as for the crosslinkable dendrimer molecule associated with the present invention, the increasing ratio of the associated body of cinnamyl residues strongly depends on the generation of the dendrimer molecule in a solid as well, as seen in a photochemical reaction behavior in a dilute solution in the above described EXample 1, and the dendrimer of the fifth-generation effectively forms a photocrosslinked body. In addition, it was judged from ultraviolet-visible absorption spectrum measurement that when the thin film of a dendrimer/poly (methyl methacrylate) after being irradiated with light is immersed in dichloromethane of a solvent used in a spin coating, the film is removed from a glass substrate.

COMPARATIVE EXAMPLE 2

Instead of the crosslinkable dendrimer used in the above described Example 2, cinnamamide was employed and diluted in poly(methyl methacrylate) to make thin films. Then the thin films were irradiated with light as in the Example 2. The results are shown in Table 6.

TABLE 6

Results of measurement of absorption spectrum after photoirradiation in solid layer of cinnamamide

| | Quantity of exposure energy (J/cm$^2$) | Trans isomer (%) | Cis isomer (%) | Associated body (%) |
|---|---|---|---|---|
| Cinnamamide | 0.2 | 80 | 19 | 1 |
| | 1.0 | 54 | 45 | 1 |
| | 5.0 | 40 | 55 | 5 |
| | 9.0 | 38 | 57 | 5 |
| | 15 | 31 | 64 | 5 |

The comparison of the above described Table 5 with the Table 6 makes it clear that in the photochemical behavior in a solid as well as in a dilute solution, the formation rate of the associated body of cinnamamide is greatly different from that of a crosslinkable dendrimer, and is extremely low.

EXAMPLE 3

Except that a polypropylene imine dendrimer molecule was solely used instead of the polypropylene imine dendrimer molecule diluted and dispersed in poly (methyl methacrylate), a similar experiment to the Example 2-1, the Example 2-2 and the Example 2-3 was performed. Though a glass substrate was immersed in dichloromethane, a film remained on the glass substrate. This occurred because in the present example, the polypropylene imine dendrimer molecular became a macromolecule insoluble in dichloromethane.

It is clear from the Example 2 and the Example 3 that in a dendrimer/poly(methyl methacrylate) diluted film a cinnamyl residue is a core of an intramolecular bonding inside one molecule of the dendrimer, and that in a dendrimer-rich thin film, an intermolecular bonding among dendrimer proceeds. In addition, it is clear that in a solid as well, a nano-particle and a nano-wire can be produced.

EXAMPLE 4-1

In a dichloromethane solution of the polypropylene imine dendrimer of the first-generation (n=1 in general formula (1) having a cinnamamide residue in the periphery of the molecule, 4,4'-bis(dimethylamino)benzophenone was each mixed as a sensitizer, and the solute was reprecipitated in a surplus quantity of hexane. The precipitate was dialyzed with dichloromethane and was reprecipitated again.

The dichloromethane solution of the polypropylene imine dendrimer of the first generation which includes 4,4'-bis (dimethylamino)benzophenone was irradiated with the light having the wavelength of 365 nm which was taken out from a mercury xenon lamp with an output of 200 W. In the above step, the temperature of the solution was room temperature.

A cinnamamide residue does not absorb light of 365 nm, but 4,4'-bis (dimethylamino)benzophenone has an absorption band in the vicinity of 365 nm. It was found from the result of ultraviolet-visible absorption spectrum measurement that the number of molecules of 4,4'-Bis(dimethylamino)benzophenone included in the dendrimer was nil for the first generation. The dichloromethane solution containing the dendrimer, which was prepared in the above described method, was thoroughly irradiated with the light of 365 nm, but no change was observed in ultraviolet-visible absorption spectra.

EXAMPLE 4-2

Except that the polypropylene imine dendrimer of the third generation (n=3 in general formula (1)) was employed, a similar experiment to the Example 4-1 was carried out to produce a molecular aggregate.

As a result of ultraviolet-visible absorption spectral measurement, it was found that the number of molecules of 4,4'-bis(dimethylamino)benzophenone included in the dendrimer was three for the third generation.

EXAMPLE 4-3

Except that the polypropylene imine dendrimer of the fifth generation (n=5 in general formula (1)) was employed, a similar experiment to the Example 4-1 was carried out to produce a molecular aggregate.

As a result of ultraviolet-visible absorption spectrum measurement, it was found that the number of molecules of 4,4'-bis(dimethylamino)benzophenone included in the dendrimer was eight for the fifth generation.

EXAMPLE 5-1

So as to make the ratio of a cinnamamide unit to a methyl methacrylate monomer unit in a dendrimer controlled to 1:10, a solution was prepared which has the photocrosslinkable dendrimer molecules (the third generation polypropylene imine dendrimer) including 4,4'-Bis(dimethylamino) benzophenone diluted and dispersed in poly(methyl methacrylate).

The poly(methyl methacrylate) solution prepared in such a method was applied onto a glass substrate with a spin coat method. The glass substrate after being coated with the solution, was dried at room temperature to form a solid containing the dendrimer thereon.

The light having the wavelength of 365 nm was taken out from a mercury xenon lamp having the output of 200 W, and the glass substrate was irradiated with the light. With progress of the photoirradiation, the absorption bands around 280 nm originating from a cinnamamide residue decreased. The absorption spectrum after the photoirradiation was measured, and the abundance ratio of each trans isomer, cis isomer and photocrosslinked body of the cinnamamide residue was calculated. The result is shown in Table 7.

EXAMPLE 5-2

Except that the polypropylene imine dendrimer of the fifth generation was employed, a similar experiment to the Example 5-1 was carried out to produce a molecular aggregate. As in the Example 5-1, the absorption spectrum after the photoirradiation was measured, and the abundance ratio of each trans isomer, cis isomer and photocrosslinked body of the cinnamamide residue was calculated. The result is shown in Table 7.

TABLE 7

Isomeric ratios in the third and fifth generation dendrimers after photoirradiation

| | Quantity of exposure energy (J/cm$^2$) | Trans isomer (%) | Cis isomer (%) | Photocrosslinked body (%) |
|---|---|---|---|---|
| Third generation | 0.1 | 76 | 13 | 11 |
| | 0.4 | 54 | 19 | 27 |
| | 1.0 | 32 | 22 | 46 |
| | 2.0 | 18 | 24 | 58 |
| | 3.0 | 13 | 24 | 63 |
| Fifth generation | 0.1 | 81 | 14 | 5 |
| | 0.4 | 63 | 17 | 20 |
| | 1.0 | 44 | 20 | 36 |
| | 2.0 | 27 | 24 | 49 |
| | 3.0 | 20 | 26 | 54 |

From a result shown in Table 7, it is clear that with photoirradiation, the formation ratio of the trans isomer of the cinnamamide residue decreased, and the formation ratios of the cis isomer and the photcrosslinked body increased.

In addition, the comparison result of the formation ratios of the photocrosslinked body of cinnamamide between the dendrimers of the third generation and of the fifth generation, made it clear that the ratio in the dendrimer of the third generation is higher than that in the dendrimer of the fifth-generation. A dendrimer including 4,4'-bis(dimethylamino)benzophenone could form a photocrosslinked body by the low exposure energy of 3.0 J/cm$^2$ in the wavelength of 365 nm. The exposure energy of 3.0 J/cm$^2$ is lower than that in producing a photocrosslinked body by directly exciting a cinnamamide residue with the light having the wavelength of 313 nm. This is considered to happen because a sensitizer absorbs light, and due to the light energy absorbed by the sensitizer, connective residues have been effectively combined (crosslinked). Thus, it can be said that the present invention, in spite of using an exposure light of low energy, has succeeded in forming a structure of single molecular highly sensitively by photocrosslinking.

EXAMPLE 5

A dendrimer/poly(methyl methacrylate) thin-film after photoirradiation was immersed in dichloromethane which is a solvent used for a spin coating. As a result, it was judged from ultraviolet-visible absorption spectrum measurement that the film is removed from the surface of the glass substrate. From the fact, it is considered that when a dendrimer dilute solution is irradiated with light, a polymer is not formed. This is considered to happen because the bonding residues in the dendrimer were combined by photoirradiation to mainly form nano-particles.

EXAMPLE 6

A thin film containing only photocrosslinkable dendrimers was fully irradiated with the light of 365 nm, and was immersed in dichloromethane as in the case described above. As a result, the film remained on a glass substrate. From the fact, it is considered that when the thin film containing only dendrimers was irradiated with light, the polymerization proceeded. This is considered to happen because a photocrosslinking reaction proceeded among dendrimer molecules by the photoirradiation, and nano-wires were mainly formed.

INDUSTRIAL APPLICABILITY

According to the present invention, a nano-particle and a nano-wire can be effectively produced.

According to the present invention, a molecular device can be adequately produced by a bottomed-up design.

A nano-particle and a nano-wire according to the present invention can be used as a liquid crystal material, a functional material, an electronic functional material, a catalyst, a nano-level electronic element, a nano-level FET, a toner raw material, additives for plastics such as an antistatic agent and a charge donor agent, and a drug delivery system.

A nano-wire according to the present invention can be used for a superdense memory material and a light emitting element, which take advantage of the periodicity of a level of a plurality of nanometers to a plurality of hundreds of nanometers.

The invention claimed is:

1. A method of producing a molecular device including:
   a step of intra-molecule bonding by crosslinking bonding residues in a molecular structure having a higher atomic density in the periphery than in the interior and having the bonding residues in the periphery;
   wherein the molecular structure is a dendrimer expressed by the following formula (I) or (II):

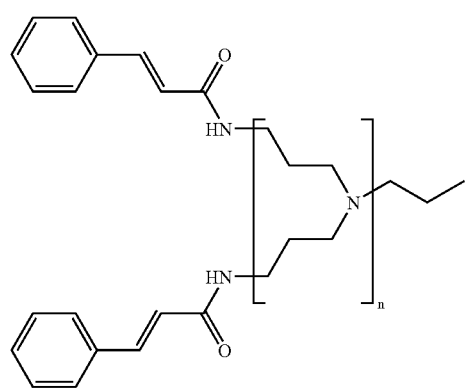

(I)

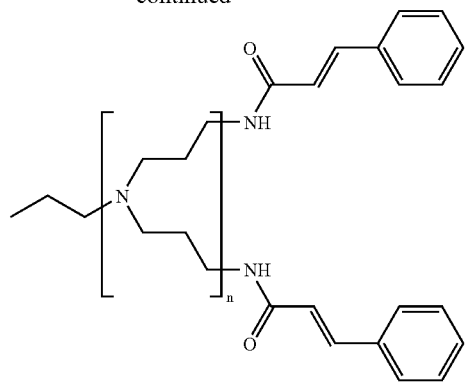

wherein n represents an integer of 10 or less, and

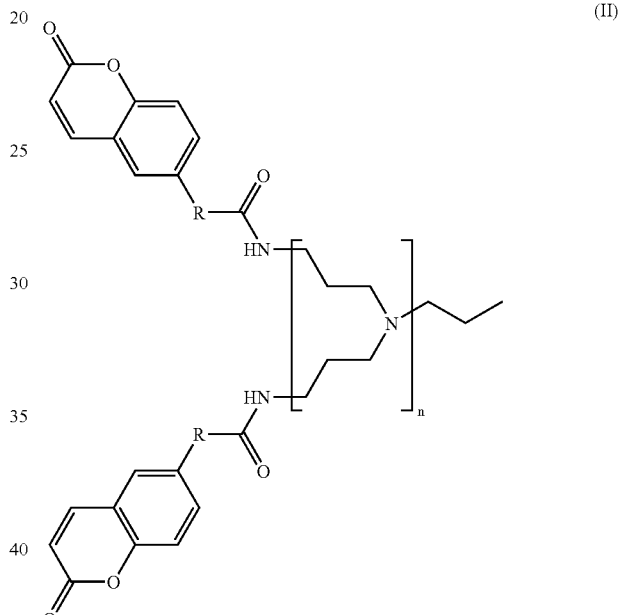

(II)

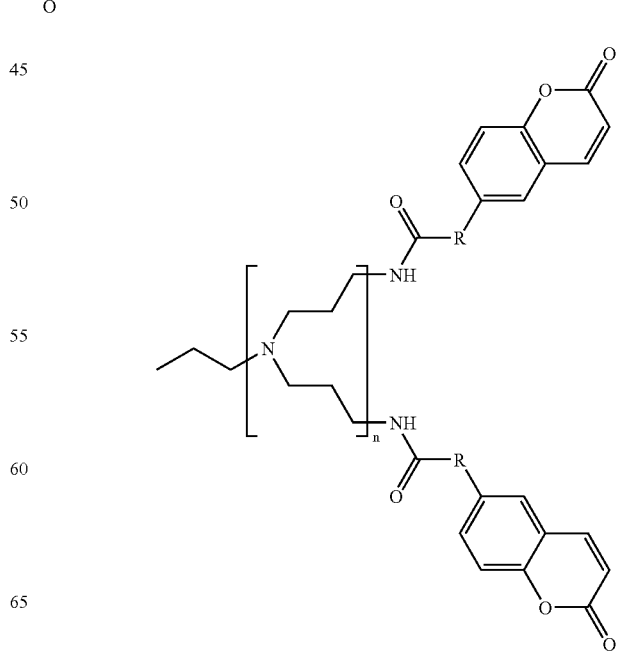

wherein n represents an integer of 10 or less and R represents a linkage group.

2. The method of producing a molecular device according to claim 1, characterized in that the molecular structure is constituted by a skeleton portion having a skeleton structure, and a terminal portion which is arranged in an outer shell of the skeleton portion, and the terminal portion has a higher atomic density than that of the skeleton portion and the terminal portion has bonding residues;

and that in the step of intra-molecule bonding by crosslinking the bonding residues, the bonding residues in the terminal portion of the molecular structure are crosslinked to form the molecular structure into a shell structure.

3. The method of producing a molecular device according to claim 2 or 1, wherein R in the general formula (II) is an alkenyl group with $C_1$ to $C_{10}$ or an alkynyl group with $C_2$ to $C_{10}$.

4. The method of producing a molecular device according to claim 2 or 1, wherein each n in the general formulas (I) and (II) is an integer of 2 to 10.

* * * * *